US012797308B2

(12) United States Patent
Scandolera et al.

(10) Patent No.: US 12,797,308 B2
(45) Date of Patent: Nov. 17, 2026

(54) SKIN TREATMENT PREPARATION

(71) Applicant: GIVAUDAN SA, Vernier (CH)

(72) Inventors: Amandine Scandolera, Pomacle (FR); Morgane De Tollenaere, Pomacle (FR); Romain Reynaud, Toulouse (FR)

(73) Assignee: GIVAUDAN SA, Vernier (CH)

( * ) Notice: Subject to any disclaimer, the term of this patent is extended or adjusted under 35 U.S.C. 154(b) by 184 days.

(21) Appl. No.: 18/721,526

(22) PCT Filed: Jan. 11, 2023

(86) PCT No.: PCT/EP2023/050544

§ 371 (c)(1),
(2) Date: Jun. 18, 2024

(87) PCT Pub. No.: WO2023/135170

PCT Pub. Date: Jul. 20, 2023

(65) Prior Publication Data

US 2025/0057737 A1 Feb. 20, 2025

(30) Foreign Application Priority Data

Jan. 13, 2022 (GB) ..................................... 2200421
Sep. 23, 2022 (GB) ..................................... 2213932

(51) Int. Cl.

| | |
|---|---|
| ***A61K 8/02*** | (2006.01) |
| ***A61K 8/25*** | (2006.01) |
| ***A61K 8/26*** | (2006.01) |
| ***A61K 8/73*** | (2006.01) |
| ***A61Q 19/00*** | (2006.01) |

(52) U.S. Cl.

CPC .............. *A61K 8/0283* (2013.01); *A61K 8/25* (2013.01); *A61K 8/26* (2013.01); *A61K 8/735* (2013.01); *A61Q 19/00* (2013.01); *A61K 2800/412* (2013.01); *A61K 2800/56* (2013.01); *A61K 2800/614* (2013.01); *A61K 2800/651* (2013.01)

(58) Field of Classification Search

CPC .. A61K 8/02883; A61K 8/0283; A61K 8/735; A61Q 19/00

See application file for complete search history.

(56) References Cited

U.S. PATENT DOCUMENTS

2021/0128442 A1* 5/2021 Lovchik ................. A61K 8/735
2022/0118154 A1* 4/2022 Wang ...................... A61L 27/26

FOREIGN PATENT DOCUMENTS

CN 111904902 A * 11/2020 ............. A61K 8/988

OTHER PUBLICATIONS

Yildiz et al. "Cosmetic investigation of the adsorption of hyaluronic acid glycolic acid on tutmac clay", J Int Environmental App & Sci, 2021, vol. 16, Iss 4, pp. 133-139. (Year: 2021).*

* cited by examiner

*Primary Examiner* — Gina C Justice
(74) *Attorney, Agent, or Firm* — Norris McLaughlin, PA

(57) ABSTRACT

A skin treatment preparation, comprising hyaluronic acid having a molecular weight of from 10-1000 KDa, absorbed into an activated smectite clay, the hyaluronic acid-clay blend having a non-pore specific surface of from 3-10 $M^2/g$ and a particle size (VSSA) of from 250-500 nm.

The application of such a treatment to the skin permits a penetration into the skin significantly deeper that either hyaluronic acid alone or a simple hyaluronic acid-clay blend.

12 Claims, 1 Drawing Sheet

SKIN TREATMENT PREPARATION

This is an application filed under 35 USC 371 based on PCT/EP2023/050544, filed on 11 Jan. 2023, which claimed priority to both GB 2200421.2, filed 13 Jan. 2022, and GB 2213932.3, filed 23 Sep. 2022. The present application claims the full priority benefit of all prior applications and incorporates by reference their full disclosures as if set forth herein.

COMPOSITION

This disclosure relates to a method of skin treatment, and to compositions for effecting such treatment.

Hyaluronic acid is a naturally-occurring glycosaminoglycan found throughout the body's connective tissue. It is the main component of what gives skin structure, and is responsible for providing a plump and hydrated look. As a result, there have emerged over recent years a substantial number of hyaluronic acid-based skin treatment preparations For the best results, it is desired that the hyaluronic acid penetrate deeply into the skin. With conventional skin creams, this has not always been possible. It has now been surprisingly found that a particular delivery means can provide unusually deep skin penetration, with concomitant improvements in skin condition. There is therefore provided a skin treatment preparation, comprising hyaluronic acid having a molecular weight of from 10-1000 KDa, absorbed into an activated smectite clay, the hyaluronic acid-clay combination having a non-pore specific surface of from 3-10 $M^2/g$ and a particle size (VSSA) of from 250-500 nm.

There is additionally provided a method of providing hyaluronic acid to the skin, the hyaluronic acid comprising part of a hyaluronic acid-clay combination as hereinabove described.

There is additionally provided an activated smectite clay into which is blended hyaluronic acid, the hyaluronic acid-clay blend having a non-pore specific surface of from 3-10 $M^2/g$ and a particle size (VSSA) of from 250-500 nm.

Volume Specific Surface-Area (VSSA) is an integral measurement method that provides an indirect representation of particle size.

Smectite clays are a group of platy phyllosilicate minerals of 2:1 layer and a layer charge from about −0.2-0.6 per formula unit. They have a large specific surface area and exhibit a high degree of swelling in water. A particular example of a smectite clay is montmorillonite, more particularly bentonite.

Combinations of hyaluronic acid ("HA") and clays are known and commercially available as part of skin-care treatments. However, it has been surprisingly found that combinations as hereinabove defined can penetrate much more deeply into the skin than can simple mixtures of HA and clay.

The parameters of the HA-clay blends of this disclosure cannot be achieved by simple mixing. The preparation of the HA-clay blend of the disclosure is carried out by applying a very high shear in a rotor/stator mixer, similar to the shear produced in an extruder reactor. Any such mixer may be used, for example ball mills, ribbon blenders, paddle blenders, screw blenders and double cone blenders.

Prior to blending, the smectite clay is activated. This may be any kind of activation known to the art, a typical example being acid activation, as described, for example by Maged et al in Environmental Science and Pollution Research, 27, pp. 32980-32997 (2020). After drying and sieving, the activated smectite clay is subjected to high shear. The shearing time will depend on the particular materials and shearing method used, but the skilled person can readily ascertain by simple experimentation a suitable duration in each case. A typical, non-limiting shearing time will be from 15 minutes to 2 hours, particularly from 30 minutes to 1 hour.

It is believed, without restricting the disclosure in any way, that pressure and shear forces have the ability to increase interactions between the clay and the HA. Moreover, under such combination of pressure (>1 bar) and shear forces, it is believed that the lamellar structure of the clay opens up, making hydroxyl groups on the platelet edges of the clay more available. It is believed, again without restricting the disclosure in any way, that the interactive mechanism is through hydrogen bonding between the hydrophilic moieties in HA (such as carboxylic acid or hydroxyl groups) and hydroxyl groups on the clay.

It is believed, again without restricting the disclosure in any way, that interaction between HA and clay confers on the HA a strongly anionic character with lower electrical potential as measured by zeta potential, which is significantly different from that of the HA alone. This electrical behavior is believed to give better skin affinity with the viable epidermis layer leading to skin penetration of HA, whereas the HA alone cannot penetrate at all. It is known that there is a natural gradient of pH in the skin, leading to the existence of more positive charges at the surface. As a result, hyaluronic acid applied alone tends to stay at or near the surface of the skin.

In particular embodiments, the specific surface is from 4-9, more particularly from 5-8 $M^2/g$. In other particular embodiments, the particle size (VSSA) is from 280-450, more particularly from 300-430 nm.

These figures are lower (for specific surface area) and higher (for particle size) because of the method of production of the HA-clay blends of this disclosure.

The activated smectite clay may be used unmodified, but in a particular embodiment, it may be modified with a fatty substance, to enhance absorption into the skin. Typical substances include oils and hydrocarbon waxes of animal or vegetable or mineral origin, silicone oils, or their mixture. Particular examples of hydrocarbon-based modifiers include vegetable and animal oils and fats, more particularly triglycerides; synthetic ethers; linear or branched hydrocarbons, of mineral or synthetic origin, such as petroleum jelly; synthetic esters such as isopropyl myristate and fatty alcohol benzoates; heptanoates, octanoates, decanoates or ricinoleates of alcohols or polyalcohols; hydroxylated esters such as isostearyl lactate, esters of polyols; fatty alcohols such as octyldodecanol; higher fatty acids such as linolenic acid; silicone oils of polymethylsiloxane type and mixtures thereof.

Examples of vegetable waxes include carnauba, candelilla, jojoba wax or any other vegetable compound consisting of an ester of ethylene glycol and of two fatty acids or of a monester of fatty acid and of long-chain alcohol; animal waxes such as beeswax. Other fatty substances and lipophilic additives include essential oils; natural aromatic compounds and lipophilic syntheses; natural or synthetic fat-soluble vitamins such as tocopherol or alphatocopheryl acetate.

The proportion of fatty substances in the clay typically varies from 0.05 to 14.5% by weight.

The hyaluronic acid of the disclosure has a molecular weight of from 10-1000 KDa, particularly from 20-1500 KDa, more particularly from 50-1400 KDa, more particularly from 100-1100 KDa, and even more particularly from 300-1000 KDa. It may be added as the acid, or as the alkali metal salt (typically sodium) with a suitable acid, such as citric acid, for generation of the acid The modified clay may be made into a skin treatment preparation by any known means. The preparation may contain all the normal ingredients of such preparations in art-recognised proportions. Non-limiting examples include vitamins, antioxidants, thickeners, trace elements, softeners, sequestering agents, perfumes, basifying or acidifying agents, preservatives, UV filters, hydrophilic or lipophilic active ingredients and mixtures thereof.

The hyaluronic acid is present in such a preparation in the weight proportion of from 5-15%, particularly from 8-12%, more particularly from 9-11%.

The surprising effect of this particular combination of the smectite clay and hyaluronic acid is that it penetrates particularly deeply into the skin. It is believed, with restricting the disclosure in any way, that the clay modifies the zeta-potential of the hyaluronic acid, making the combination more negatively charged. It is known that there is a natural gradient of pH in the skin, leading to the existence of more positive charges at the surface. As a result, hyaluronic acid tends to stay at or near the surface of the skin. However, the negative charge imparted by the clay allows the deeper penetration into the skin, with resulting beneficial effects.

An additional unexpected and surprising benefit is the enhancement of a feeling of well-being among people to whose skin a preparation according to the disclosure has been applied. This benefit has been scientifically verified by a testing procedure further described in the examples.

The disclosure is further described with reference to the following non-limiting figures and examples.

EXAMPLE 1

Testing in a Skin Cream

(a) Preparation of Hyaluronic Acid-Clay Blend

Figure 1:
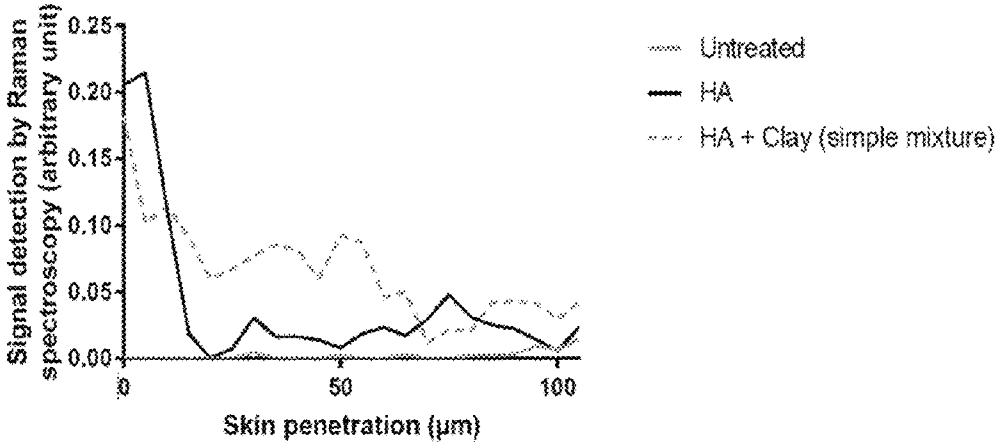
FIG. 1 is a graphical representation of the depth penetration into the skin of hyaluronic acid when applied alone, and in a simple blend with clay, as available commercially.

The hyaluronic acid-clay blend was prepared by taking a commercially-available bentonite clay, activating it by the method described by Maged et al in Environmental Science and Pollution Research, 27, pp. 32980-32997 (2020), drying and sieving it using a 100 μm filter, adding to it sodium hyaluronate and then shearing this mixture in a high-shear ribbon blender for one hour

(b) Preparation of Test Skin Creams

Two test skin creams were prepared by blending the following ingredients

| | Cream 1 | Cream 2 |
|---|---|---|
| water | 87.1 | 88.1 |
| Emulium ™ Delta MD* | 5.0 | 5.0 |
| Isodecyl neopentonate | 4.5 | 4.5 |
| HA clay | — | 1 |
| glycerin | 1 | 1 |
| phenoxyethanol | 1 | 1 |

-continued

| | Cream 1 | Cream 2 |
|---|---|---|
| dimethicone | 0.3 | 0.3 |
| fragrance | 0.1 | 0.1 |

*Commercially-available emulsifier (ex Gattefossé)

(c) Testing of Creams

The test subjects were 20 women in the age range 35-55, all of whom had dry skin and who had shallow wrinkles and crow's feet. They were split into two groups, designated Group A and Group B. Group A applied Cream 1, whereas Group B applied Cream 2.

All subjects applied the creams twice daily, morning and evening, on the face. The skin was examined immediately prior to first application, then at 1 hour, 6 hours, 7 days and 28 days. Examination was by means of a Visia™ CR2.3 visual scanner (ex Canfield Scientific), which measured the area of the crow's feet. The results are shown in the following table:

| | % reduction in crow's feet area after . . . | | | |
|---|---|---|---|---|
| Test subjects | 1 hour | 6 hours | 7 days | 28 days |
| Group A | 1.1 | 5 | 6.9 | 4.6 |
| Group B | 18.5 | 21.5 | 16.1 | 27.3 |

Thus, the improvement provided by Cream 1 is 17.4% after 1 hour, 16.5% after 6 hours and 22.7% after 28 days.

EXAMPLE 2

Demonstration of the skin penetration of hyaluronic acid when used in a blend prepared according to this disclosure.

The following materials were tested:

Untreated clay ("untreated")

Hyaluronic acid (HA)

HA+clay ("simple mixture")

HA-clay blend according to this description ("HA Clay")

HA was used in distilled water at 1% by weight, and both simple mixture and HA Clay were used at 10% in distilled water, both containing 1% by weight of hyaluronic acid.

Human skin explants from a 47 years old donor were prepared and kept in survival medium (MIL215001, Biopredic) for 24 hours at 37° C. and 5% $CO_2$. The next day, HA Clay and HA were topically applied and incubated for 8 hours at 37° C. and 5% $CO_2$ before skin penetration analysis. An untreated sample was used as a control. After the end of incubation, the skin surface was cleaned in order to eliminate any excess of the product. The skin explants were then frozen at −80° C. and cut longitudinally using a cryotome with a thickness of 20 μm. For each explant, 3 tissue sections were selected and deposited on a $CaF_2$ support for Raman imaging analysis for a total of 9 Raman images per condition. 3 other adjacent sections of 7 μm thickness were prepared for an Hematoxylin & Eosin staining.

The Raman images had a size of Y: 10 μm/X: 100 μm with a step of 5 μm in X and 5 μm in Y. Each Raman image has 3Y spectra and 21X spectra (63 spectra per image).

Laser wavelength: 600 nm

Objective: 100×, long focal length with a numerical aperture 0.75

Acquisition time: 25 seconds

Accumulation: 1×

Spectral range: 400 to 4000 $cm^{-1}$
Gratting: 950T
Confocal Hole: 300 μm
Slit width: 150 μm (spectral resolution 6.5 $cm^{-1}$)
Step in X: 5 μm, Step in Y: 5 μm In order to ensure reproducibility of the measurements, before each use, the Raman spectrometer was calibrated with silicon which gives a Raman peak at 520.7 $cm^{-1}$. Continuous control of the laser power at the sample level was achieved.

A pre-processing of Raman images was made by eliminating aberrant spectra (fluorescence, burning, saturation), correcting the baseline, applying a spectral smoothing and despike and a spectral normalization.

The processing of corrected data maps was performed by using software based on least squares fitting method that operates with Matlab software. This method involved mathematical modelling of reference spectra in the overall spectral image to determine the contribution and distribution of these spectra within the image. In this study, the average spectra of hyaluronic acid and clay were used as reference spectra.

Figure 2:
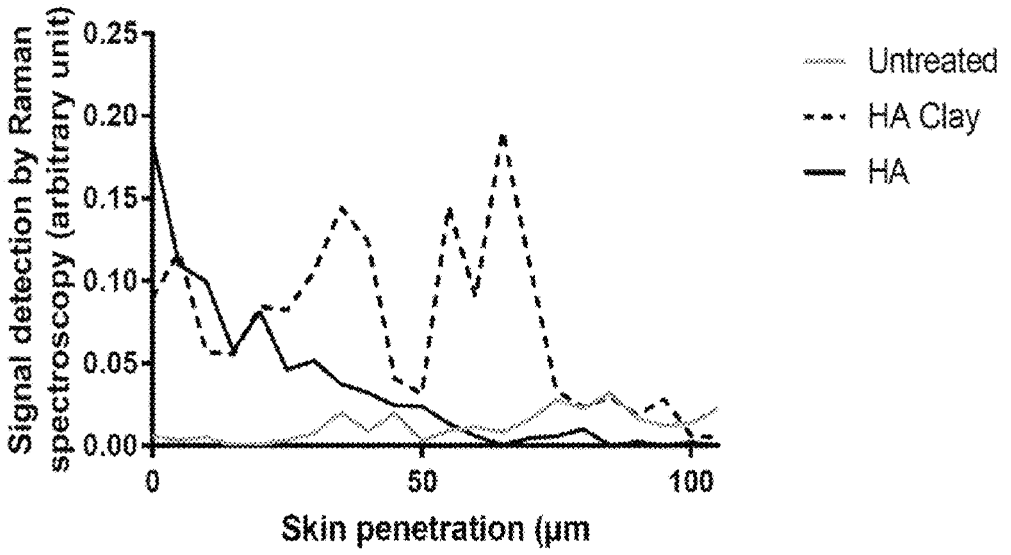
FIG. 2 is a repeat of FIG. 1, but with the simple clay-hyaluronic acid blend replaced by a hyaluronic acid-clay blend as described in this disclosure.

It can be seen from FIGS. 1 and 2 that the penetration into the skin of the HA Clay is considerably deeper than either the HA alone or the simple mixture. The clay alone has very little penetration into the skin, showing conclusively that the HA Clay combination produced according to this disclosure gives much deeper skin penetration formulae are shown below, Cream 3 being the cream with the hyaluronic acid/clay blend and Cream 4 the placebo

| | | Cream 3 | Cream 4 |
|---|---|---|---|
| A | Water | To 100% | To 100% |
| | cross-linked polyacrylic acid homopolymer[1] | 0.5 | 0.5 |
| | 1,2-hexanediol/1,2-octanediol blend[1] | 0.3 | 0.3 |
| | phenoxyethanol | 0.5 | 0.5 |
| B | 30.5% sodium hydroxide | To pH 7 | To pH 7 |
| C | Caprylocaproyl Macrogolglycerides[2] | 1 | 1 |
| | C8/C10 medium-chain triglycerides[3] | 5 | 5 |
| D | Hyaluronic acid/clay | 1 | 0 |
| | water | 4 | 0 |
| Viscosity[5] | | 15,000 | 8,000 |

[1]Carbopol ™ ETD 2050 ex Lubrizol
[2]Symdiol ™ 68, ex Symrise
[3]Dubcare ™ GPE 810 ex Stearinerie Dubois
4 Miglyol ™ 812N ex IOI Oleo GmbH
[5]viscosity in mPa · s (Brookfield DVIII Ultra, Spindle F, speed 12 @ 20° C.)

(b) Testing of Skin Creams

Testing was performed on 59 subjects, 42 women and 17 men, average age 38, all ordinary members of the public. Testing was double-blind, in that the testers also did not know which of Cream 3 or Cream 4 was being presented to the test subject.

Testing was performed by the subjects applying the product on the hands on 2 consecutive days. The test subjects were asked to complete the questionnaire shown on the following page before and after the testing. The questionnaire was presented on a computer screen and each question was accompanied by a slider that could be moved to present a position between "Not at all" (value=0) and "Very" (value=10). A representation of the screen is shown below.

| | [Not at all] | [Very] |
|---|---|---|
| How MOTIVATED do you feel RIGHT NOW? | ● | ● |
| How INTERESTED do you feel RIGHT NOW? | ● | ● |
| How SATISFIED do you feel RIGHT NOW? | ● | ● |
| How OPTIMISTIC do you feel RIGHT NOW? | ● | ● |
| How FRUSTRATED do you feel RIGHT NOW? | ● | ● |
| How INVIGORATED do you feel RIGHT NOW? | ● | ● |
| How FATIGUED do you feel RIGHT NOW? | ● | ● |
| How RESTLESS do you feel RIGHT NOW? | ● | ● |
| How HAPPY do you feel RIGHT NOW? | ● | ● |
| How BORED do you feel RIGHT NOW? | ● | ● |
| How CALM do you feel RIGHT NOW? | ● | ● |
| How RELAXED do you feel RIGHT NOW? | ● | ● |
| How EXCITED do you feel RIGHT NOW? | ● | ● |
| How SAD do you feel RIGHT NOW? | ● | ● |
| How MENTALLY ALERT do you feel RIGHT NOW? | ● | ● |
| How STRESSED do you feel RIGHT NOW? | ● | ● |
| How ANXIOUS do you feel RIGHT NOW? | ● | ● |
| How PATIENT do you feel RIGHT NOW? | ● | ● |

EXAMPLE 3

Demonstration of an enhanced feeling of well-being experienced by recipients of a composition as hereabove described.

(a) Preparation of Skin Cream

Two skin creams were prepared, one containing a hyaluronic acid/clay blend prepared according to Example 1, the other without the blend and used as a placebo. The A well-being metric was used for this study to measure the effects of the test cream on the well-being of test subjects. The well-being metric, described in detail in International Publication WO 2020/165463, to which reference may be made, was defined by applying experimental psychology and unsupervised clustering of verbal attributes of well-being in order to identify the most relevant dimensions to assess well-being. The well-being attributes take into account various aspects of well-being, such as affective, eudaimonic, social, and physical aspects. These aspects may have both affective (emotional) and cognitive (rational) components.

The weighting of the well-being attributes was determined as follows:

a) Having one or more human subject(s) assess their well-being in the absence of a test cream by providing a well-being score $wb_i$ for each of the WB-18 attributes;

b) Applying a factor analysis, in particular a principal component analysis, on the well-being scores obtained in step a), in order to determine the impact of each well-being attribute on the overall well-being, resulting in M well-being factors $F_j$;

i) wherein each of the well-being factors $F_j$ has a variance $v_j$ expressed as a percentage of the sum of the variances of all well-being factors;

ii) wherein each of the well-being factors $F_j$ comprises a finite number $n_j$ of well-being attributes, having a loading $l_i$, expressed as a percentage of the sum of the $n_j$ loadings; and iii) wherein none of the well-being attributes appears in more than one well-being factor; and c) Calculating the well-being score in the absence of the test perfume according to the following equation $$WB_0 = \sum_1^M v_j F_{j,0} = \sum_1^M v_j \sum_1^{n_j} l_i wb_i$$

The principal component analysis revealed that:

the well-being attributes "not anxious", "not sad", "not restless", "not frustrated", "not stressed" are associated with a first well-being factor $F_1$ having a variance $v_1$;

the well-being attributes "happy", "optimistic", "excited", "satisfied", "motivated", "invigorated" are associated with a second well-being factor $F_2$ having a variance $v_2$;

the well-being attributes "interested" and "not bored" are associated with a third well-being factor $F_3$ having a variance $v_3$;

the well-being attributes "not fatigued" and "mentally alert" are associated with a fourth well-being factor $F_4$ having a variance $v_4$;

the well-being attributes "calm", "relaxed", and "patient" are associated with a fifth well-being factor $F_5$ having a variance $v_5$;

the variance $v_1$ is 48% of the sum of the variances of all well-being factors;

the variance $v_2$ is 24% of the sum of the variances of all well-being factors;

the variance $v_3$ is 12% of the sum of the variances of all well-being factors;

the variance $v_4$ is 9% of the sum of the variances of all well-being factors; and the variance $v_5$ is 7% of the sum of the variances of all well-being factors.

It was further found that each attribute had a loading within each factor ($F_1$, $F_2$, $F_3$, $F_4$, $F_5$) as listed in Table 1

TABLE 1

| well-being attribute | weight | well-being attribute | weight |
|---|---|---|---|
| "not anxious" | 10.65% | "motivated" | 3.34% |
| "not sad" | 10.32% | "invigorated" | 3.31% |
| "not restless" | 9.84% | "interested" | 6.12% |
| "not frustrated" | 9.65% | "not bored" | 5.88% |
| "not stressed" | 7.54% | "not fatigued" | 4.59% |
| "happy" | 4.70% | "mentally alert" | 4.41% |
| "optimistic" | 4.61% | "calm" | 2.66% |
| "excited" | 4.13% | "relaxed" | 2.24% |
| "satisfied" | 3.91% | "patient" | 2.10% |

Using this methodology, the numerical results from the tests were summed to provide a mean for each attribute for each cream, and then these individual attribute scores were summed to provide an overall well-being score for each cream.

The overall well-being results are shown in Table 2:

TABLE 2

| Overall Well-being | | | | | |
|---|---|---|---|---|---|
| Cream | time | #people | Well_Being | DeltaWell_Being | p-value* |
| 4 | Before | 59 | 6.62767 | . | |
| 4 | After | 59 | 7.03020 | .40253 | 0.0002 |
| 3 | Before | 59 | 6.78831 | . | |
| 3 | After | 59 | 7.36640 | .57809 | <.0001 |

*significant difference in average well-being between time points for this sample at 5% level (using per product ANOVA model).

The results for the positive well-being attributes (excited, happy, invigorated, motivated, optimistic, satisfied) before and after application are shown in Table 3

TABLE 3

| | | | Positive Well-being Attribute Mean Scores - Factor 2 | | | | | |
|---|---|---|---|---|---|---|---|---|
| Cream | time | #people | Excited | Happy | Invigorated | Motivated | Optimistic | Satisfied |
| 4 | Before | 59 | 3.01695 | 6.87797 | 4.68644 | 6.52373 | 6.75763 | 6.57627 |
| 4 | After | 59 | 2.96610 | 7.01695 | 5.52542 | 6.66949 | 6.76271 | 6.58305 |
| 3 | Before | 59 | 3.71695 | 7.08475 | 5.15763 | 7.18814 | 6.99492 | 6.74068 |
| 3 | After | 59 | 3.28136 | 7.29153 | 6.42034 | 7.64407 | 7.52373 | 7.72712 |

Cream 3 has higher mean scores for all of the individual positive attributes, both before and after application The overall scores from Table 3 are summed in Table 4:

TABLE 4

| Cream | time | #People | Factor 2 | Delta Factor 2 | Significance Tukey |
|---|---|---|---|---|---|
| 4 | Before | 59 | 5.78873 | | |
| 4 | After | 59 | 5.94533 | 0.15660 | b |
| 3 | Before | 59 | 6.17936 | | |
| 3 | After | 59 | 6.64491 | 0.46555 | a |

This shows that Cream 3 provides a significantly higher change in perception of well-being than does Cream 4

The overall result was that, of the 59 test subjects, 46 experienced an enhanced feeling of well-being when tested with Cream 3, that is, 78% of the subjects experienced a feeling of enhanced well-being as a result of exposure to the cream containing the hyaluronic acid, as hereinabove described. The overall before and after scores for the test subjects with respect to cream 3 are in Table 5.

TABLE 5

| id | time | Well_Being |
|---|---|---|
| 2 | Before | 5.57092 |
| 2 | After | 7.94589 |
| 3 | Before | 5.99631 |
| 3 | After | 7.69726 |
| 4 | Before | 5.65649 |
| 4 | After | 5.79497 |
| 5 | Before | 7.76163 |
| 5 | After | 8.25730 |
| 6 | Before | 7.87110 |
| 6 | After | 8.44446 |
| 7 | Before | 8.64540 |
| 7 | After | 9.06027 |
| 8 | Before | 6.34506 |
| 8 | After | 6.87326 |
| 9 | Before | 6.78824 |
| 9 | After | 7.18967 |
| 10 | Before | 4.31721 |
| 10 | After | 5.23760 |
| 11 | Before | 5.58852 |
| 11 | After | 5.78647 |
| 12 | Before | 8.43674 |
| 12 | After | 9.12289 |
| 13 | Before | 7.50836 |
| 13 | After | 8.06117 |
| 15 | Before | 8.72271 |
| 15 | After | 8.75911 |
| 16 | Before | 4.43377 |
| 16 | After | 6.19799 |
| 18 | Before | 3.67135 |
| 18 | After | 6.23457 |
| 19 | Before | 6.80760 |
| 19 | After | 7.41274 |
| 20 | Before | 8.34265 |
| 20 | After | 8.76346 |
| 22 | Before | 6.35522 |
| 22 | After | 7.43166 |
| 23 | Before | 7.58404 |
| 23 | After | 7.95747 |
| 24 | Before | 5.09373 |
| 24 | After | 5.94184 |
| 26 | Before | 6.20437 |
| 26 | After | 8.10128 |
| 27 | Before | 6.53698 |
| 27 | After | 6.64062 |
| 28 | Before | 4.42279 |
| 28 | After | 5.84135 |
| 29 | Before | 6.72004 |
| 29 | After | 7.43519 |
| 30 | Before | 6.91288 |
| 30 | After | 7.16838 |
| 31 | Before | 7.88311 |
| 31 | After | 8.01820 |
| 33 | Before | 7.49052 |
| 33 | After | 7.71904 |
| 34 | Before | 6.99532 |
| 34 | After | 7.77377 |
| 35 | Before | 6.11921 |
| 35 | After | 6.63916 |
| 37 | Before | 6.77235 |
| 37 | After | 7.37346 |
| 38 | Before | 4.92260 |
| 38 | After | 6.91941 |
| 40 | Before | 6.15231 |
| 40 | After | 7.06477 |
| 41 | Before | 8.31633 |
| 41 | After | 8.54854 |
| 42 | Before | 5.22997 |

TABLE 5-continued

| id | time | Well_Being |
|---|---|---|
| 42 | After | 6.08023 |
| 43 | Before | 5.16520 |
| 43 | After | 9.00050 |
| 44 | Before | 6.35405 |
| 44 | After | 7.00782 |
| 45 | Before | 8.14190 |
| 45 | After | 9.17455 |
| 47 | Before | 9.29376 |
| 47 | After | 9.45334 |
| 48 | Before | 5.00783 |
| 48 | After | 5.27916 |
| 51 | Before | 8.00264 |
| 51 | After | 8.85107 |
| 53 | Before | 5.25018 |
| 53 | After | 7.02882 |
| 54 | Before | 5.20258 |
| 54 | After | 6.92175 |
| 55 | Before | 6.40573 |
| 55 | After | 7.11388 |
| 56 | Before | 3.09843 |
| 56 | After | 3.98142 |
| 57 | Before | 7.22005 |
| 57 | After | 7.43451 |
| 59 | Before | 7.25772 |
| 59 | After | 7.94343 |

The invention claimed is:

1. A skin treatment preparation, comprising hyaluronic acid having a molecular weight of from 10-1000 KDa, absorbed into an activated smectite clay, the hyaluronic acid-clay blend having a non-pore specific surface of from 3-10 $M^2/g$ and a particle size (VSSA) of from 250-500 nm.

2. A skin treatment preparation according to claim 1, in which the non-pore specific surface is from 4-9 $M^2/g$ and the particle size (VSSA) is from 280-45 nm.

3. A skin treatment preparation according to claim 2, in which the non-pore specific surface is from 4-9 $M^2/g$ and the particle size (VSSA) is from 300-430 nm.

4. A skin treatment preparation according to claim 1, in which the molecular weight of the hyaluronic acid is from 20-1500 KDa.

5. A skin treatment preparation according to claim 1, in which the activated smectite clay is montmorillonite.

6. A skin treatment preparation according to claim 1, in which the activated smectite clay is used in an unmodified form.

7. A skin treatment preparation according to claim 1, in which the activated smectite clay is modified with a fatty substance.

8. A skin treatment preparation according to claim 7, in which the fatty substance is selected from the group consisting of: oils and waxes of animal, vegetable or mineral origin, silicone oils, and mixtures thereof.

9. A skin treatment preparation according to claim 4, in which the molecular weight of the hyaluronic acid is from 50-1400 KDa.

10. A skin treatment preparation according to claim 9, in which the molecular weight of the hyaluronic acid is from 100-1100 KDa.

11. A skin treatment preparation according to claim 10, in which the molecular weight of the hyaluronic acid is from 300-1000 KDa.

12. A skin treatment preparation according to claim 5, in which the activated smectite clay is bentonite.

* * * * *